United States Patent
Chen et al.

(10) Patent No.: US 10,258,037 B2
(45) Date of Patent: *Apr. 16, 2019

(54) USE OF LIPO CHITOOLIGOSACCHARIDES TO INITIATE EARLY FLOWERING AND FRUIT DEVELOPMENT IN PLANTS AND RELATED METHODS AND COMPOSITIONS

(71) Applicant: NOVOZYMES BIOAG A/S, Bagsvaerd (DK)

(72) Inventors: Chunquan Chen, Cambridge (CA); Ewa Maria Cholewa, North Bay (CA); John David McIver, Dundas (CA); Birgit Carolyn Schultz, Lancaster (CA); Yang Yang, Guelph (CA)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,462

(22) Filed: May 18, 2015

(65) Prior Publication Data

US 2016/0309714 A1    Oct. 27, 2016

Related U.S. Application Data

(63) Continuation of application No. 13/788,408, filed on Mar. 7, 2013, now abandoned, which is a continuation of application No. 10/554,028, filed as application No. PCT/CA2004/000606 on Apr. 22, 2004, now Pat. No. 8,415,275.

(60) Provisional application No. 60/464,455, filed on Apr. 22, 2003.

(51) Int. Cl.
*A01N 43/16* (2006.01)
*A01N 63/02* (2006.01)

(52) U.S. Cl.
CPC ............. *A01N 43/16* (2013.01); *A01N 63/02* (2013.01); *Y02A 40/143* (2018.01)

(58) Field of Classification Search
None
See application file for complete search history.

(56) References Cited

U.S. PATENT DOCUMENTS

| 5,175,149 A | 12/1992 | Stacey |
| 5,549,718 A | 8/1996 | Lerouge |
| 8,415,275 B2 | 4/2013 | Chen |

FOREIGN PATENT DOCUMENTS

| EP | 0427094 A1 | 10/1990 |
| WO | 00/04778 A1 | 2/2000 |
| WO | 01/04778 A2 | 1/2001 |
| WO | 01/26465 A1 | 4/2001 |
| WO | 01/56381 A1 | 8/2001 |
| WO | 01/56382 A1 | 8/2001 |
| WO | 01/56384 A1 | 8/2001 |
| WO | 2004/093542 A1 | 11/2004 |

OTHER PUBLICATIONS

Atti et al., Irrig. and Drain, 54:15-30 (2005).
Bonnell et al., Database Geneseq [Online] XP-002288410, Accession No. 2003:117350.
International Search Report dated Jul. 26, 2004.
International Preliminary Report on Patentability dated Jul. 25, 2005 for International Application No. PCT/CA2004/000606.
Written Opinion of the International Searching Authority dated Jul. 25, 2005 for International Application No. PCT/CA2004/000606.
Prithiviraj et al., Planta, 216:437-445 (2003).
Chento Lin, Plant Physiology 123:39-50 (2000).
Oh et al., HortScience 44(2):341-344 (2009).
Terfa et al., Physiol Plant 148(1):146-159 (2013) abstract only.
Atti et al, 2002, 18th International Congress on Irrigation and Drainage.
Atti et al, 2003, CABA International database accession No. 20033101040.

*Primary Examiner* — Alton N Pryor
(74) *Attorney, Agent, or Firm* — Adam Rucker

(57) ABSTRACT

The present invention relates to the use of LCOs in initiating earlier flowering, increased number of buds and flower buds and earlier fruit development in non legume and legume plants, as compared to flowering and fruit development under conditions without use of LCOs, and the enhancement of plant growth and yield associated therewith; to compositions comprising an effective amount of at least one LCO and agriculturally acceptable carriers, associated with earlier flowering, increased bud and flower numbers and earlier initiation of fruit development as compared to conditions without use of LCOs, and with increased growth and plant; and to methods using LCOs and compositions of one or more LCOs and agriculturally acceptable carriers, associated with earlier flowering, increased bud and flower numbers and earlier fruit development in both legume and non-legume crop plants as compared to conditions without use of LCOs and associated enhancement of growth and yield.

21 Claims, 16 Drawing Sheets

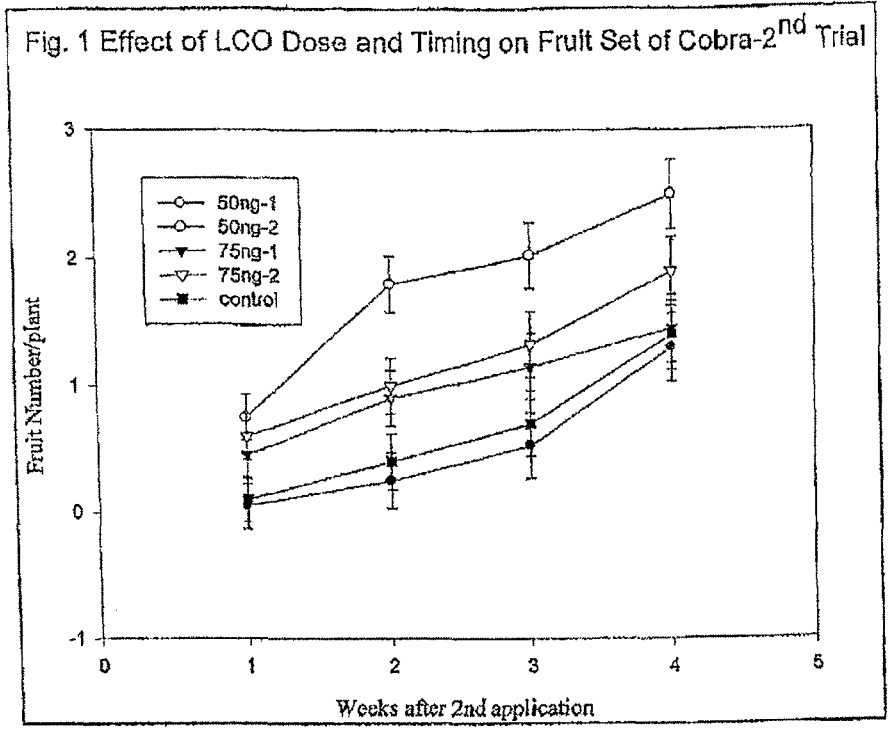
Fig. 1 Effect of LCO Dose and Timing on Fruit Set of Cobra-2$^{nd}$ Trial
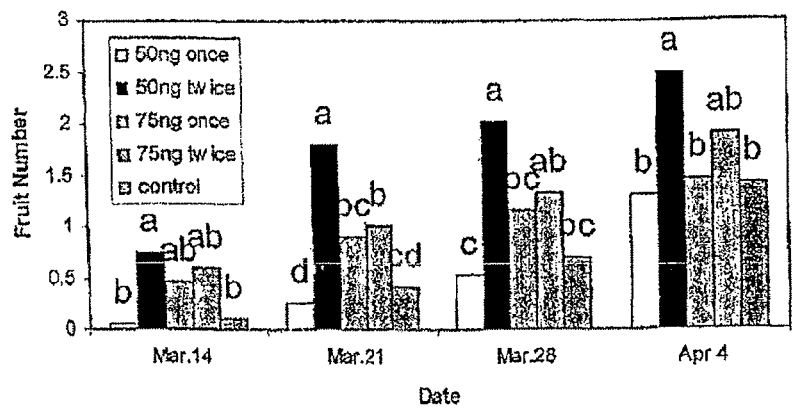
Fig. 2 Significant Effect of LCO Dose and Timing on Fruit Number of Greenhouse Tomatoes (Cobra)

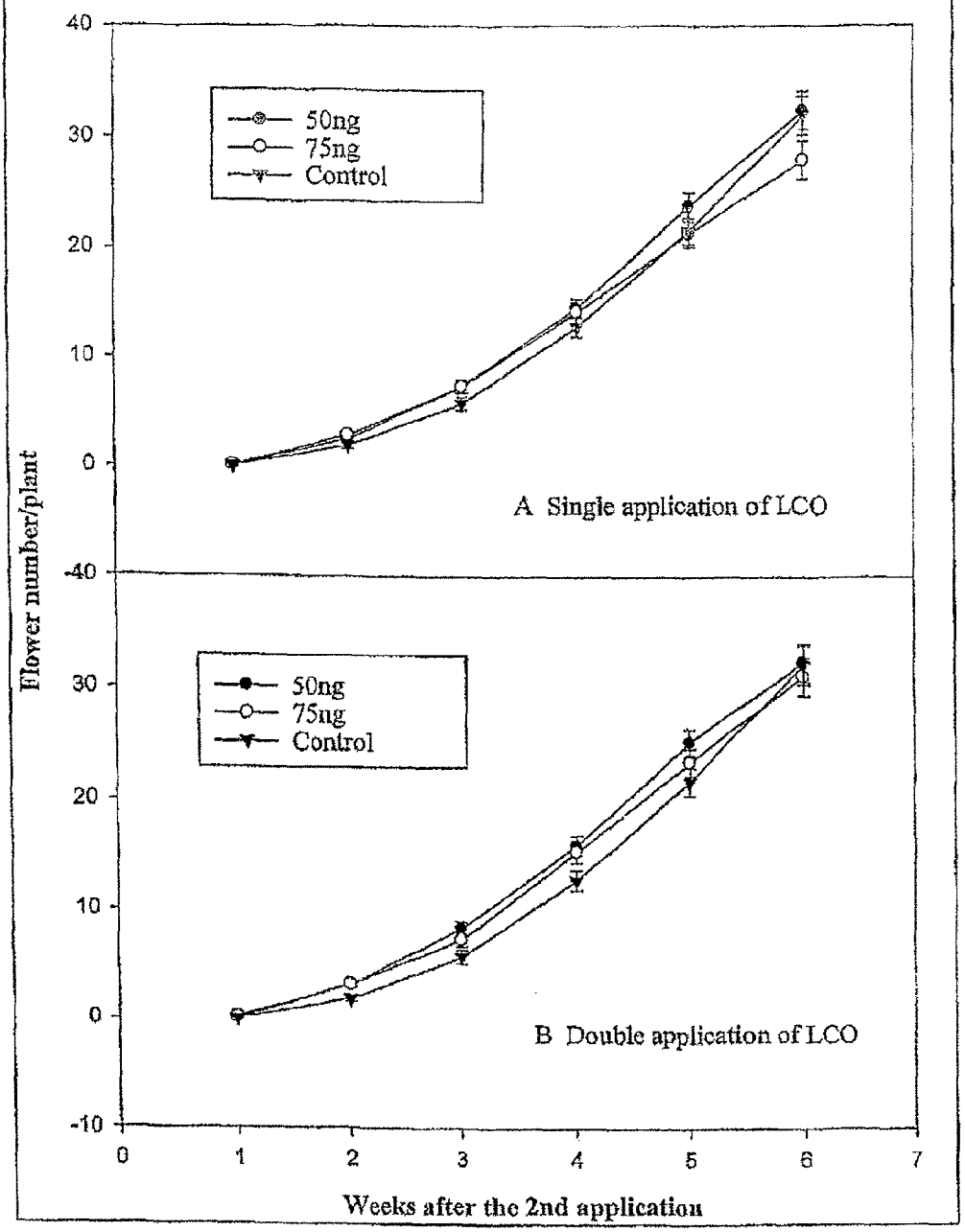

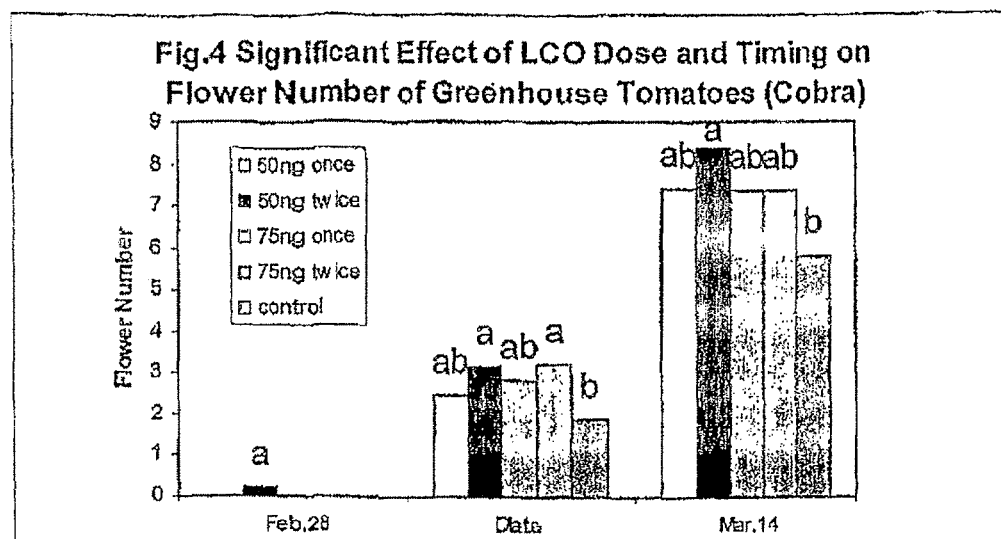
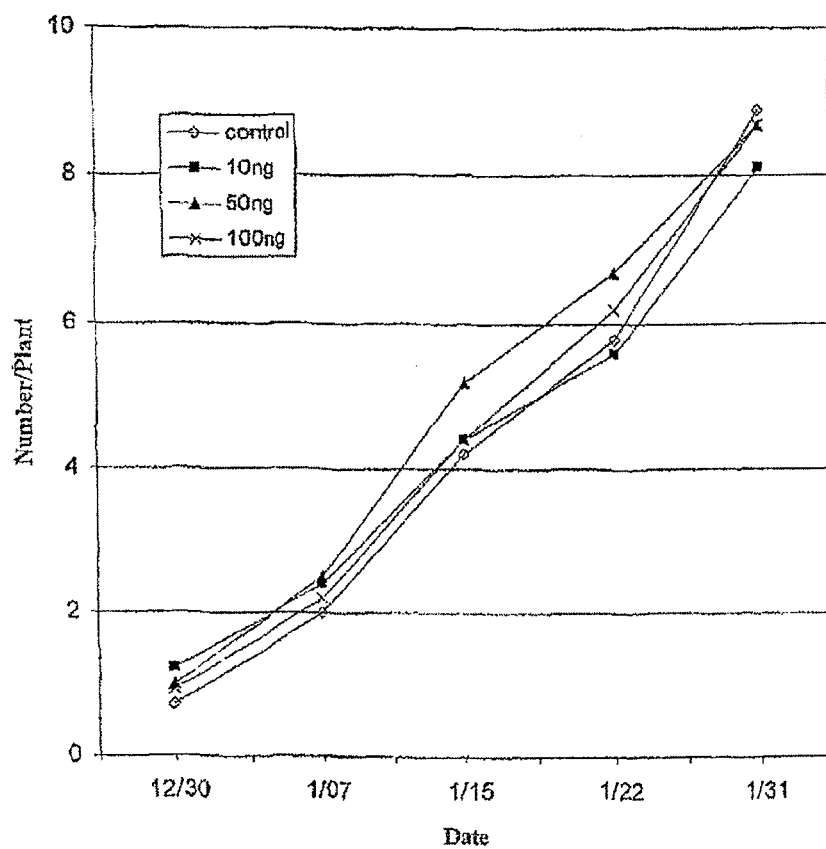

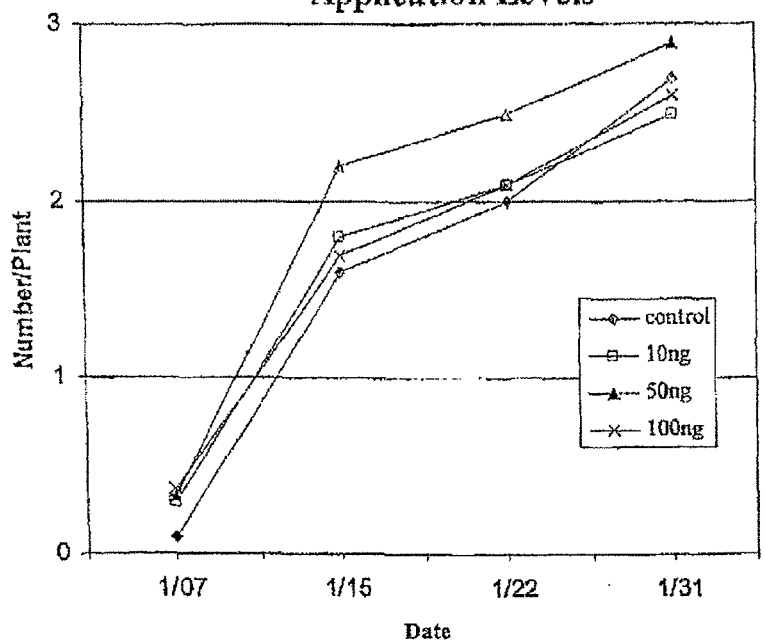

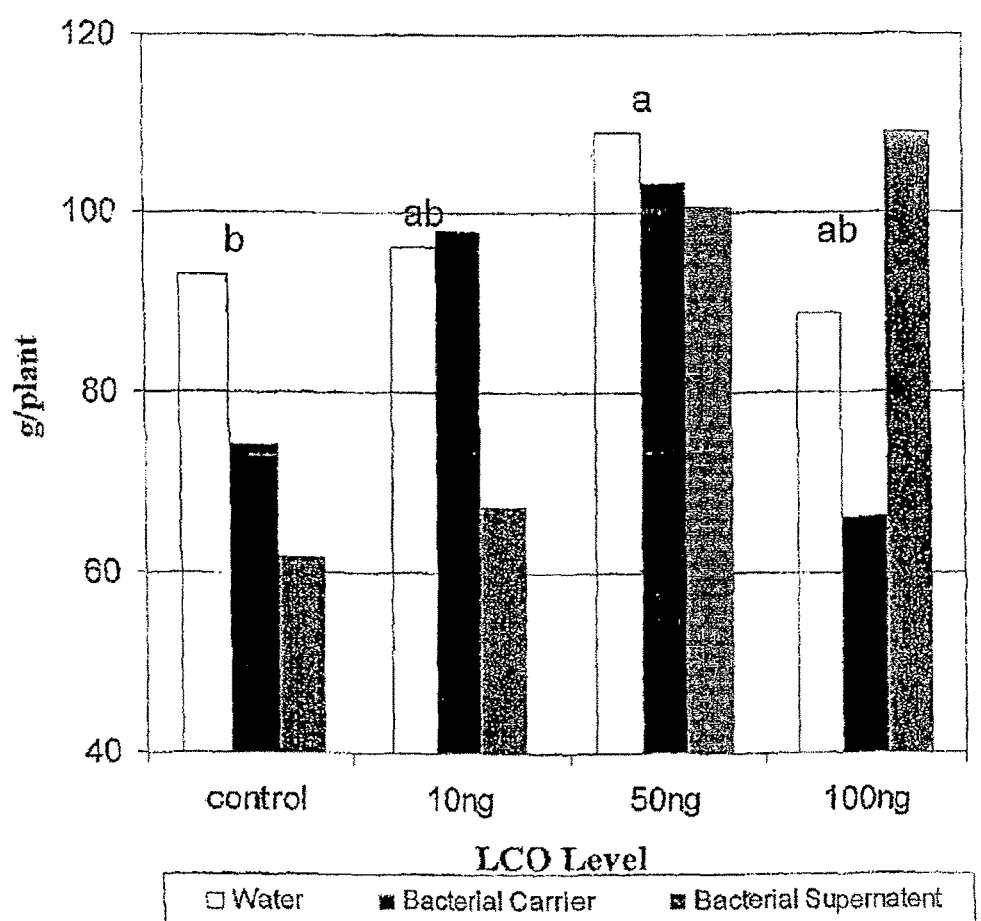
Fig. 7 Early Yield of Cobra Greenhouse Tomatoes on Jan. 31

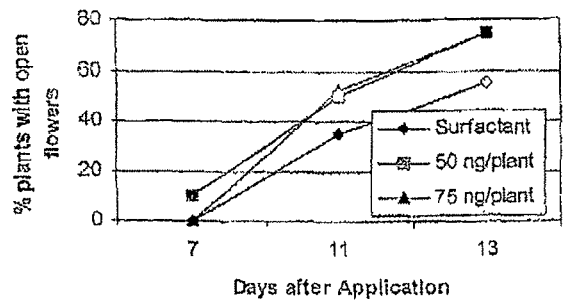
Fig. 8 LCO Foliar Application Advanced Flowering of Greenhouse Tomatoes
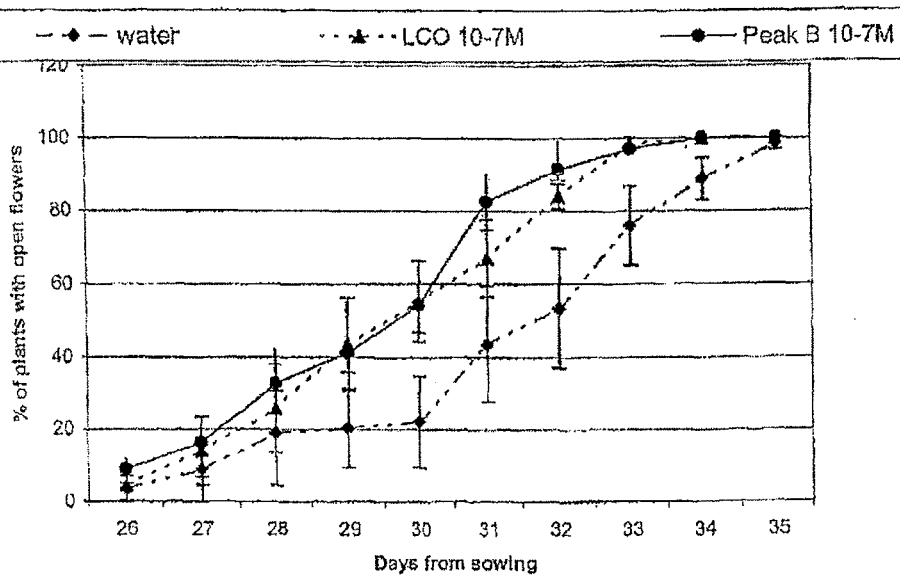
Fig. 9 Induction of flowering in *Arabidopsis thaliana*

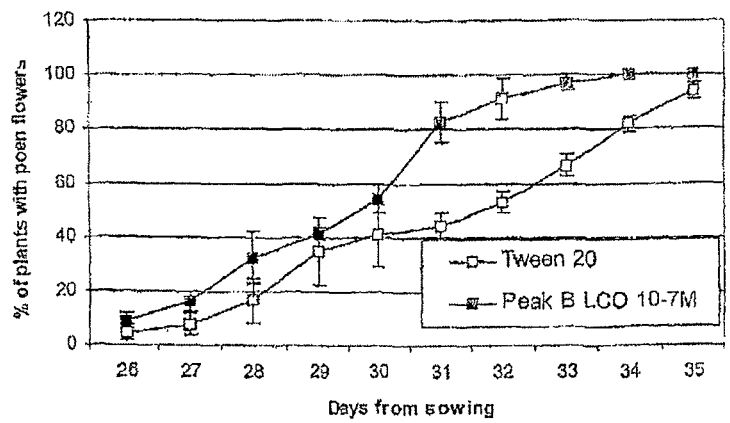

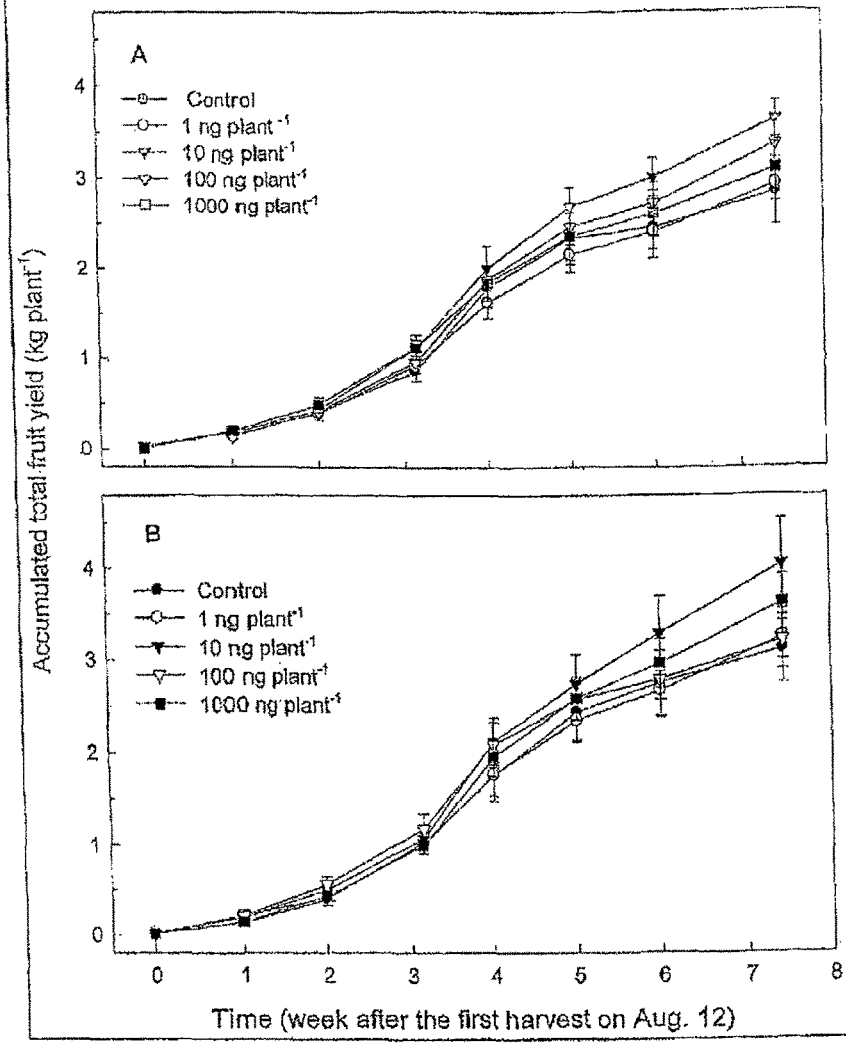
Fig. 11 Effects of LCO spary on tomato yield in field experiment A, single application; B, double application
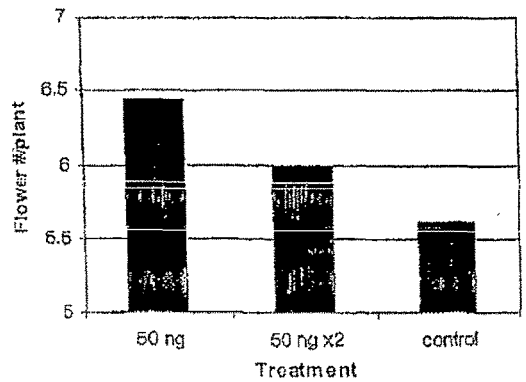
Fig 2-1. LCO foliar application enhanced early flowering and total flower number in greenhouse tomatoes

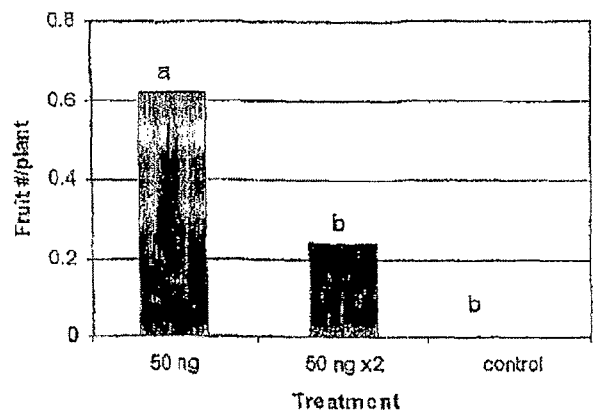

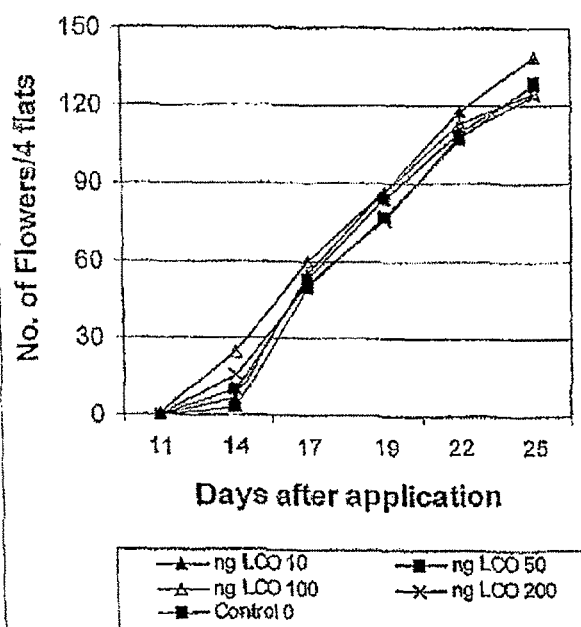

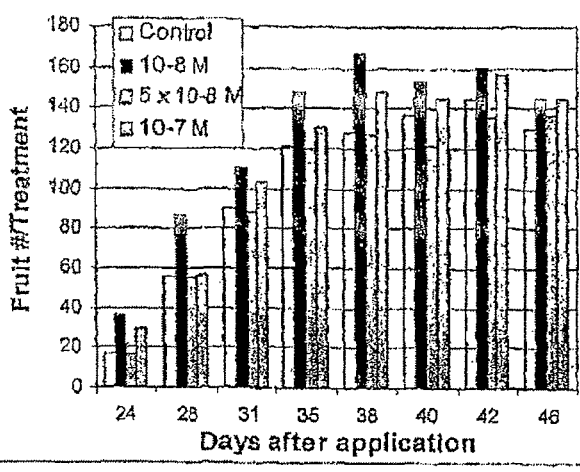

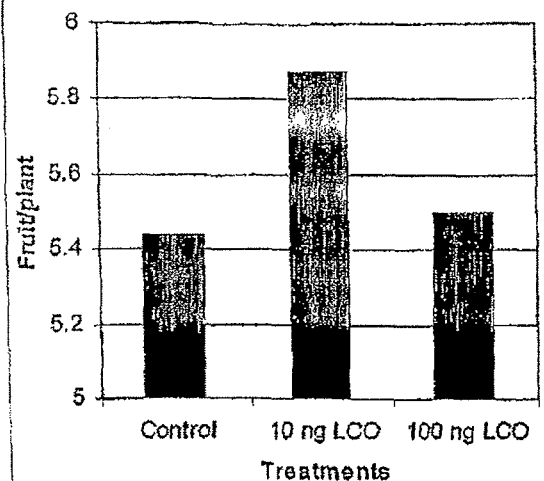
Fig. 2-5 Effect of LCO soil application on cherry tomato early fruit numbers
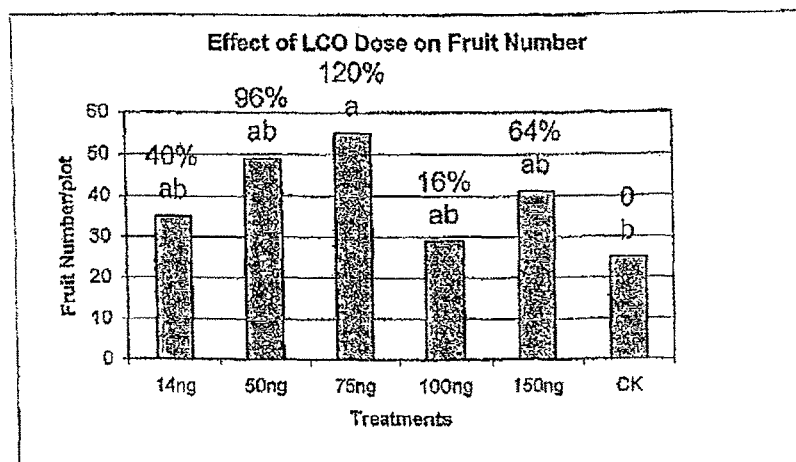
Fig 2-6. LCO application promoted tomato early fruit number Fig. 2-7 LCO application promoted tomato early fruit
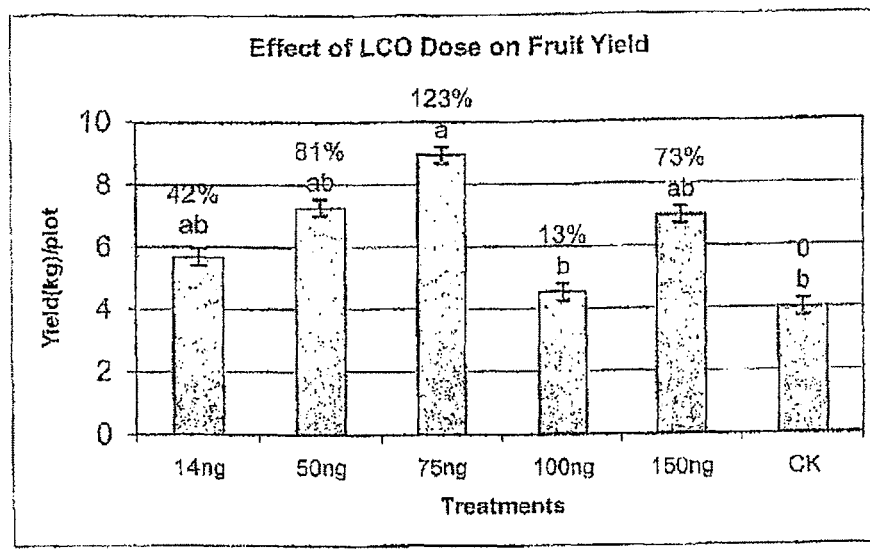

Fig 2-8 Cumulative harvested fruit number from tomato plants when 50ng/plant LCO was applied once at variable growing stages
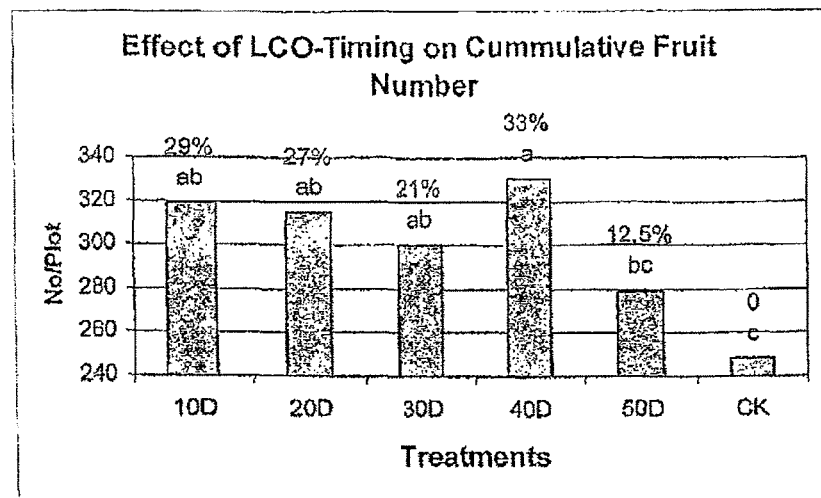
Fig 2-9 Cumulative harvested fruit yield from tomato plants when 50ng/plant LCO was applied once at variable growing stages
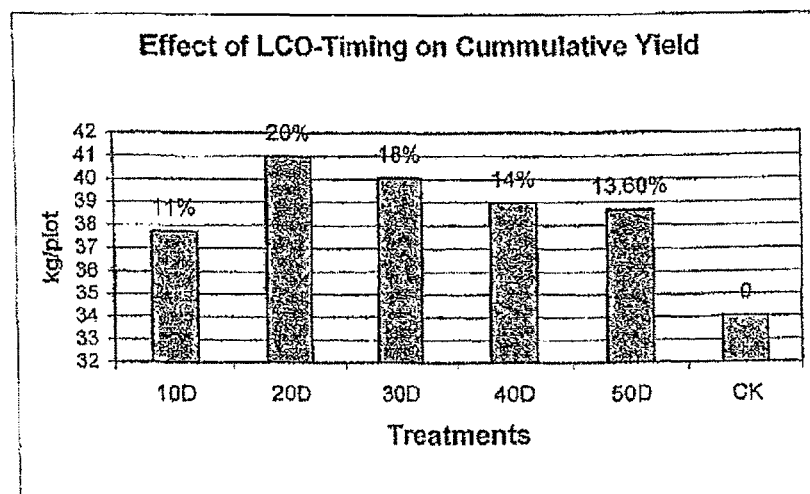

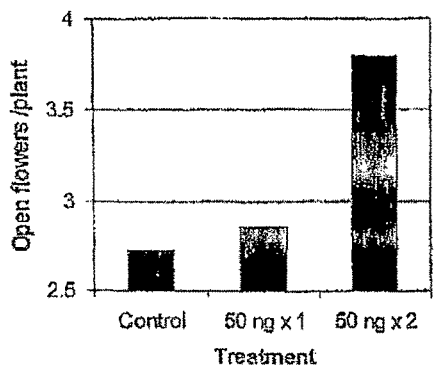
Fig. 2-10 Effect of LCO application on advancement of hot pepper early flowering
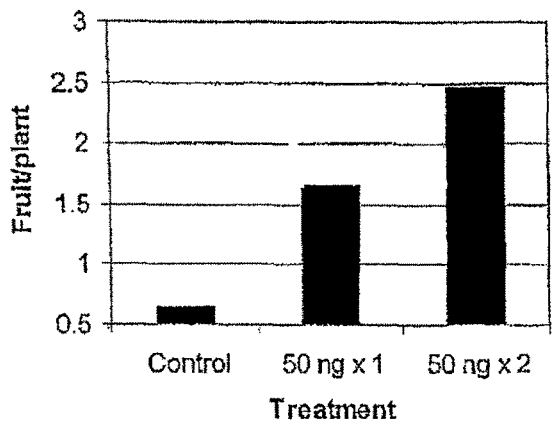
Fig. 2-11 Effect of LCO application on advancement of hot pepper fruiting

USE OF LIPO CHITOOLIGOSACCHARIDES TO INITIATE EARLY FLOWERING AND FRUIT DEVELOPMENT IN PLANTS AND RELATED METHODS AND COMPOSITIONS

CROSS-REFERENCE TO RELATED APPLICATIONS

This application is a continuation of U.S. patent application Ser. No. 13/788,408 filed Mar. 7, 2013, pending, which is a continuation application of U.S. patent application Ser. No. 10/554,028, filed Jun. 30, 2006, now U.S. Pat. No. 8,415,275, which is a U.S. National Phase Application under 35 U.S.C. § 371 of International Patent Application No. PCT/CA2004/000606, filed Apr. 22, 2004, which claims priority to U.S. Provisional Patent Application No. 60/464,455, filed Apr. 22, 2003, the contents of all of which are incorporated by reference in their entireties for all purposes.

FIELD OF THE INVENTION

The present invention relates generally to the fields of horticulture including but not limited to flowers, fruits, vegetables, nuts, turfgrass, herbs, spices, ornamental shrubs and trees, aquatic plants and mushrooms grown outdoors or in greenhouses or indoors for both commercial or personal use and agriculture and more specifically to the use of Lipo-chitooligosaccharides (LCDs) and compositions thereof to induce early flowering, increase the number of buds and flowers, initiate earlier fruiting, earlier maturity and increase yields in plants and to methods of inducing earlier flowering and initiation of earlier fruiting in plants by exposure to LCOs and compositions of same.

BACKGROUND OF THE INVENTION

There is a growing interest in the role of LCOs and compositions thereof for enhancement of plant seed germination, seedling emergence and growth of plants both for crop and horticultural purposes in both legumes and non-legumes. Compositions for accelerating seed germination and plant growth are provided in Application No. PCT/CA99/00666, published Feb. 3, 2000, WO 00/04778, all contents of which are incorporated herein by reference. There is also an interest in the possible effects of LCOs in plant photosynthesis and PCT/CA00/01192, published Apr. 19, 2001, WO 01/26465 A1 describes the use of LCOs and compositions of LCOs for increasing plant photosynthesis. Chemical structures of LCOs are described in U.S. Pat. Nos. 5,175,149; 5,321,011 and 5,549,718. Synthetic LCOs are also known.

There is great interest in the field of agricultural research, particularly in the field of plant growth promoters, of plant physiological processes which may be affected by LCOs. Prithiviraj et al, Planta (2003) 216:437-445 discuss certain observed induced physiological changes in both host and non-host plants by LCOs, all contents of which is incorporated herein by reference.

LCOs are known to be released by *Rhizobia*, symbiotic bacteria primarily of the genera *Generarhizobium, Bradyrhizobium, Sinorhizobium, Mesorhizobium* and *Azorhizobium* and the like, the Rhizobiacese family being in a state of taxonomic flux. Both of the aforesaid International applications summarize current understanding of the specialized symbiotic relationship of *Rhizobia* with legume host plants in the formation of nodule organs and associated fixation of atmospheric nitrogen within these organs, as well as the plant to bacteria signal and bacteria to plant signal interaction associated with such symbiotic relationship.

Although there is a considerable body of knowledge on the influence of LCOs on typical host plant physiology, there is a growing interest in the effect of LCOs on plant growth with respect to both host and non-host plants, particularly by application of the molecule without necessarily the fostering of a micro-organism and plants symbiotic relationship.

The body of knowledge relating to the possible role of LCOs, in both host and non-host plants and on processes associated with plant growth promotion continues to grow, with particular practical interest in the effects of LCOs on plant physiology and processes relevant to increase plant yields, not only with respect to commonly considered crop plants, both host and non-host, but also with respect to horticulture species.

Thus, there continues to be a need to study the effects of LCOs on plant growth, in addition to processes relating to nodulation and nitrogen fixation in legume host plants and to germination, emergence and photostimulation in both legume and non-legume plants. In particular, there is a need to study the effect of LCOs on bud and flowering initiation, budding, fruiting initiation and development, generally in relation to growth and maturity of plants, both leguminous and non-leguminous and the affect on plant yields. The present invention endeavours to address these and other needs.

SUMMARY OF THE INVENTION

The present invention relates to the use of LCOs in initiating early flowering and budding, increased flowering and budding and earlier fruit development in non-legume and legume plants, as compared to flowering and fruit development under conditions without use of LCOs, and the enhancement of plant growth and yield associated therewith. The present invention also relates to agricultural compositions comprising an effective amount of at least one LCO and agriculturally acceptable carriers, associated with early flowering and budding, increased flowering and budding, earlier plant maturity and earlier initiation of fruit development as compared to conditions without use of LCOs, and with increased growth and plant yield. The present invention further relates to methods using LCOs and compositions of one or more LCOs and agriculturally acceptable carriers, associated with earlier flowering initiation and budding, increased flowering and budding and earlier plant maturity and earlier fruit development in both legume and non-legume crop plants as compared to conditions without use of LCOs and otherwise associated enhancement of growth and yield, and all as exemplified herein below.

Surprisingly, the compositions of the present invention affect not only legume varieties but also a wide and divergent variety of non-legume plants, including crop plants and horticultural and bedding plant species in the initiation of earlier flowering and budding, increased flowering and budding, earlier maturity and earlier fruit development, and increased yield, as compared to conditions where LCOs are not applied and all as exemplified herein below.

According to the present invention, in both legume and non-legume plants, the administration of an effective amount of LCO or LCOs, or of composition of one or more LCOs with agriculturally suitable carriers, initiates buddy and/or flowering at an earlier stage, increases total bud and/or flower numbers and also causes earlier fruit development and plant maturity as compared to conditions without use of LCOs, including an associated increase in yield.

Administration of LCOs for such purpose may be by leaf or stem application, or application in the proximity of the seed, root or plant. Such methods are non-limiting and may include other methods, which would be understood by the skilled person, including by administration of micro-organisms known to release LCOs in the proximity of a plant seed, or seedling in any stage of emergence, or in the proximity of a plant, including in the vicinity of the root and root hairs. The same would be with respect to application of LCOs independent of the micro-organisms known to release such molecules.

Thus, in accordance with a further embodiment of the present invention, there is provided a method for the initiation of earlier flowering, increased budding and flowering and earlier fruit development and plant maturity in non-legume and legume plants associated with the growth and yield of a plant, comprising the treatment of a plant with an effective amount of one or more LCOs or a composition comprising an agriculturally effective amount of one or more LCOs in association with an agriculturally suitable carrier or carriers, wherein the effective amount has the effect of initiating earlier flowering and/or budding and/or increased bud and/or flower number and/or earlier fruit development and/or plant growth and/or yield, as compared to an untreated plant, and all as exemplified herein below. Suitable LCOs for use according to the present invention include the LCOs as identified in the aforesaid International applications and patents.

Compositions of the present invention will be understood to include in their scope, one or more different LCO molecules, as well as comprising one or more types of molecules other than LCO, including, without limitation, one or more plant to bacteria molecule and/or other molecules or agents known to promote growth or fitness and mixtures of such compositions.

The inventors and applicant herein are the first to show, as exemplified in the greenhouse and field experiments set out hereafter, that a composition comprising an LCO can have a significant affect on both legume and non-legume plants by initiating early bud and/or flowering, increased bud and/or flowering and earlier fruit development and/or yield, as compared to conditions without use of LCOs, and the enhancement of plant maturity, growth and yield associated therewith. Non-limiting examples of crop plants include dicotyledons and monocotyledons and legumes. From the aforesaid experiments and as set out below, it can be predicted that such results will apply to crop, horticultural and personal use plants, legumes and non-legumes, including, but not limited to, flowers, fruits, vegetables, nuts, tubers, turf grass, herbs, spices, ornamental shrubs and trees, aquatic plants and mushrooms grown in field or greenhouse for agricultural, commercial and personal use. In view of the plants exemplified herein and the results, the skilled person will appreciate, can adapt the teaching of the present invention to a diversity of plants, both legume and non-legume, for crop, horticultural and personal use, including but not limited to, plants of the families: Fabaceae, Brassicaceae, Solonaceae, Chenopodiaceae, Asteraceae, Malvaceae, Cucurbitaceae and Poaceae.

The term "LCO" as used herein, will be understood as reference in general to a Nod factor which is under control of at least one modulation gene common to *rhizobia*, that is bacterial strains which are involved in a nitrogen fixing symbiotic relationship with a legume, and which serve as micro-organism-to-plant phytohormones which induce the formation of nodules in legumes and enable the symbiotic microorganisms to colorize said plant modules. LCOs are understood to comprise derivatives of an oligosaccharide moiety, including fatty acid condensed at one end thereof. Non-limiting examples of LCOs are described in U.S. Pat. Nos. 5,175,149; 5,321,011 and 5,549,718. The instant invention is demonstrated in particular with LCOs from *Bradyrhizobium japonicum*, but it not so limited.

The uses, compositions and methods of the present invention will be understood to include initiation of early bud and/or flowering and/or increased flowering and/or budding and/or earlier fruit development and/or enhanced plant maturity and/or plant growth and yield under both sub optimal or limiting and non-limiting environmental conditions associated therewith. Such sub optimal or limiting environmental conditions include but are not limited to liming or sub optimal conditions of heat, water pH, soil nitrogen concentrations and the like.

An effective amount of LCO will be understood to relate to uses, compositions and methods of the present invention wherein the amount is sufficient to manifest statistically significant earlier budding and/or flowering and/or increased flowering and/or budding and/or earlier fruit development and/or enhanced maturity and/or plant growth and yield associated therewith.

By proximity of seed, root or plant will be understood to relate to any location of seed, root or plant wherein soluble materials or compositions of the present invention will be in actual contact with said seed, root or plant.

By bud or budding will be understood conditions consistent with stem swelling consisting of overlapping immature leaves or petals. By flowering will be understood the process or state of producing one or more flower.

BRIEF DESCRIPTION OF THE DRAWINGS

The invention having been generally described above, the accompanying figures will now be referenced in the discussion of a preferred embodiment of the invention, as set out in the examples which follow, in which:

FIG. 1 shows the effect of LCO dose and timing on fruit set of Cobra tomatoes; (Same data as table 2)

FIG. 2 shows the effect of LCO dose and timing on fruit number of Cobra tomatoes; (Same data as table 2)

FIG. 3 shows the effect of LCO dose and timing on flower number of Cobra tomatoes; (Same data as table 1)

FIG. 4 shows the effect of LCO dose and timing on flower number of Cobra tomatoes; (Same data as table 1)

FIG. 5 shows the effect of LCO dose on number of flower of Cobra tomatoes; (Same data as table 3)

FIG. 6 shows the effect of LCO dose on the number of fruit of Cobra tomatoes; (Same data—as table 4)

FIG. 7 shows the effect of LCO dose on yield of fruit of Cobra tomatoes; (Same data as table 5)

FIG. 8 shows the effect of LCO on tomato plant flowering;

FIG. 9 shows the effect of LCO on induction of flowering in *Arabidopsis thaliana;*

FIG. 10 shows the effect of LCO on induction of flowering in *Arabidopsis thaliana;*

FIG. 11 shows the effect of LCO dose on the yield of fruit per plant, in tomato plant application.

FIG. 2-1: LCO foliar application enhanced early flowering and total flower number in greenhouse tomatoes.

FIG. 2-2: LCO foliar application enhanced early fruiting and total fruit number in greenhouse tomatoes.

FIG. 2.3: Effect of LCO application on earlier flowering and number of flowers in Marigolds.

FIG. 2.4: Effect of LCO application on fruit number of strawberries.

FIG. 2.5: Effect of LCO soil application on cherry tomato early fruit numbers.

FIG. 2.6: LCO application promoted tomato early fruit number.

FIG. 2.7: LCO application promoted tomato early fruit.

FIG. 2.8: Cumulative harvested fruit number from tomato plants when 50 ng/plant LCO was applied once at variable growing stages.

FIG. 2.9: Cumulative harvested fruit yield from tomato plants when 50 ng/plant LCO was applied once at variable growing stages.

FIG. 2.10: Effect of LCO application on advancement of hot pepper early flowering.

FIG. 2.11: Effect of LCO application on advancement of hot pepper fruiting.

Figure 12A:
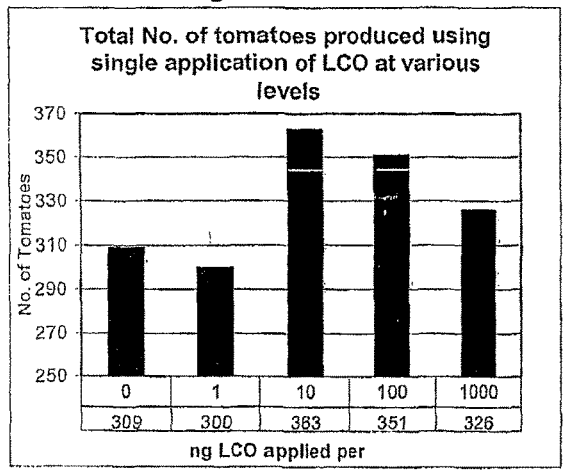
FIGS. 12A and 12B show (A) Total No. of tomatoes produced using single application of LCO at various levels, and (B) Total No. of tomatoes produced using double application of LCO at various levels.

Other objects, advantages and features of the present invention will become more apparent upon reading of the following description of preferred embodiments, which is non-restrictive, and with reference to the accompanying figures, which is exemplary and should not be interpreted as limiting the scope of the present invention.

DESCRIPTION OF THE PREFERRED EMBODIMENT

The following experiments are reported herein, conducted to study the effect of application of LCO on the initiation of flowering and fruit development of a host plant under both greenhouse and field conditions.

Trials 1 and 2: Effect of LCO on Greenhouse Tomato

Two experiments on the application of LCO to Tomatoes have been undertaken

Trial 1:

Cobra (a hybrid cultivar) was used to examine optimum application dose between 10 and 100 ng/plant at one or two applications and the LCO delivery medium. The levels chosen were the extremes of beneficial doses determined previously in tomato field trials. The delivery media tested were LCO in water, Apex and centrifuged Apex. The first application of LCO was made 10 days after transplanting. When applied a second time it was 2 weeks after the first application.

The following parameters were tested: leaf number, plant height, number of cluster, number of flower, number of fruit. Observations were made continuously for approximately a two-month period, at one-week intervals until plant growth was limited by pot bound roots.

A statistically significant difference in early yield was noted between 50 ng LCO treatment applied twice and the untreated control (see Table 5, FIG. 7, Fruit weight). Other levels of application were not significantly better in yield than control. There was statistically significant effect between 50 ng LCO treatment and control on fruit weight of Cobra. 50 ng treatment showed more uniform results in different delivery media. The increase of early yield by 50 ng LCO showed the potential ability of LCO applied as a growth enhancer on tomatoes.

There was no statistical difference between treatments on flower number and number of fruit set at any time point. However, the double application of 50 ng LCO per plant provided a numerically higher flower number earlier and also delivered the best early yield. Similarly, there was no significant difference on number of fruit among LCO treatments. Fruits appeared 48 days after transplanting and 38 days after first application of treatments and 24 days after second application of treatments. Plants in LCO 10 ng treatment showed slightly higher number of fruit than other treatments and than control.

Examination of the first graph in Trial 1 (FIG. 5, Table 3) indicates a 4-5 day advance of flowering over control and the second graph demonstrates an 8-9 day advance in early fruiting over control (horizontal separation between treatment lines). Early fruiting must arise from earlier flowering.

There was no significant difference on number of flowers among LCO treatments. Flower buds appeared 30 days after transplanting and 20 days after first application of treatments. Flowers started to open 40 days after transplanting, and 30 days after first application of treatments. The plants in 50 ng LCO treatment had more flowers than other treatments and control at 21% and 14% on January 15 and January 22. On the other days, the number of flower was similar among treatments and control.

Trial 2: The Cobra variety was used to re-examine optimal doses of LCO. The concentrations tested were 50 ng and 75 ng LCO per plant, applied once (2 weeks after transplanting) and twice (4 weeks after transplanting). The sample number was increased to 20 plants.

At 50 ng/plant there was a significant difference from control on number of flowers over the first three observations (Table 1) (see Dose & timing on Flower No. Cobra Trial 2). Later, treatment significance on flowering was lost but this is to be expected because of the flowering characteristics of the tomato plant. Examination of the Flower number data for Cobra Trial 2, (FIGS. 3 and 4) indicates an advance in flowering of some 3 days for 50 ng treatment attaining same flower number as control. On fruit number the 50 ng LCO treatment applied twice showed significantly higher numbers over control for the first 4 weeks. The higher fruit number (Table 2) (see histogram for Fruit number Cobra Trial 2) arises from earlier flowering. The graph for Dose and Timing on Fruit Set Cobra Trial 2 (FIGS. 1 and 2) demonstrates that a 50 ng/plant application twice, advances equivalent fruit numbers by 2 weeks over control.

TABLE 1

The Effect of Different LCO Concentrations on Flower Number of Cobra Tomatoes in Greenhouse Studies

| Treatments | Flower Number/ Plant (Feb. 28) | Flower Number/ Plant (Mar. 7) | Flower Number/ Plant (Mar. 14) | Flower Number/ Plant (Mar. 21) | Flower Number/ Plant (Mar. 28) | Flower Number/ Plant (April 4) |
|---|---|---|---|---|---|---|
| LCO 50 ng once | 0.0 b | 2.5 ab | 7.4 ab | 14.55 | 23.95 | 32.45 |
| LCO 50 ng twice | 0.2 a | 3.2 a | 8.4 a | 16.0 | 25.15 | 32.2 |
| LCO 75 ng once | 0.0 b | 2.85 ab | 7.35 ab | 14.2 | 21.4 | 28.0 |
| LCO 75 ng twice | 0.0 b | 3.25 a | 7.35 ab | 15.4 | 23.35 | 31.0 |
| Surfactant 500 ppm once | 0.0 b | 1.9 b | 5.8 b | 12.85 | 21.65 | 32.0 |
| Significance* | $P = 0.0006$ | $P = 0.03$ | $P = 0.05$ | $P = 0.168$ | $P = 0.156$ | $P = 0.368$ |

*There is significant different when $P < 0.05$
Notes;
Seeding: Jan. 6, Transplanting: Feb. 7, First Application: Feb. 21, Second Application: Mar. 7, 2003
(Greenhouse Tomato Cobra)

TABLE 2

The Effect of Different LCO Concentrations on Fruit Number of Cobra Tomatoes in Greenhouse Studies

| Treatments | Fruit Number/ Plant (Mar. 14) | Fruit Number/ Plant (Mar. 21) | Fruit Number/ Plant (Mar. 28) | Fruit Number/ Plant (April 4) |
|---|---|---|---|---|
| LCO 50 ng once | 0.05 b | 0.26 d | 0.525 c | 1.3 b |
| LCO 50 ng twice | 0.75 a | 1.8 a | 2.025 a | 2.5 a |
| LCO 75 ng once | 0.45 ab | 0.9 bc | 1.15 bc | 1.45 b |
| LCO 75 ng twice | 0.6 ab | 1.0 b | 1.325 ab | 1.9 ab |
| Surfactant 500 ppm once | 0.1 b | 0.4 cd | 0.7 bc | 1.4 b |
| Significance* | $P = 0.03$ | $P < 0.0001$ | $P < 0.0001$ | $P = 0.01$ |

*There is significant different when $P < 0.05$
Notes:
Seeding: Jan. 6, Transplanting: Feb. 7, First Application: Feb. 21, Second Application: Mar. 7, 2003.

Results: Effect of LCO Dose on Greenhouse Tomato (Cobra)

The cobra seedlings were transplanted 32 days after seeding, the first application was 10 days thereafter, the second application was 14 days after the first application. The fruits were harvested 6 weeks after the second application.

Results: Effect of LCO Dose on Greenhouse Tomato (Cobra)

TABLE 3

Number of Flowers/Plant

| Treatment | Dec. 30 | Jan. 7 | Jan. 15 | Jan. 22 | Jan. 31 |
|---|---|---|---|---|---|
| Control | 0.7 | 2 | 4.2 | 5.8 | 8.9 |
| 10 ng | 1.2 | 2.4 | 4.4 | 5.6 | 8.1 |
| 50 ng | 0.97 | 2.5 | 5.2 | 6.7 | 8.7 |
| 100 ng | 0.9 | 2.2 | 4.4 | 6.2 | 8.7 |
| Mean | 0.9425 | 2.275 | 4.55 | 6.075 | 8.6 |

There was no significant difference on number of flowers among LCO treatments. Flower buds appeared 30 days after transplanting and 20 days after first application of treatments. Flowers started to open 40 days after transplanting, and 30 days after the first application of treatments. The plants with a 50 ng LCO treatment had more flowers than other treatments and control at 21% and 14% on January 15 and January 22.

TABLE 4

Number of Fruit/Plant

| Treatments | Jan. 7 | Jan. 15 | Jan. 22 | Jan. 31 |
|---|---|---|---|---|
| Control | 0.1 | 1.6 | 2 | 2.7 |
| 10 ng | 0.3 | 1.8 | 2.1 | 2.5 |
| 50 ng | 0.33 | 2.2 | 2.5 | 2.9 |
| 100 ng | 0.37 | 1.7 | 2.1 | 2.6 |
| Mean | 0.275 | 1.825 | 2.175 | 2.675 |

Notes;
See Table 3 above.

LCO application at all levels advanced early fruit set, three to four weeks after application. The optimal application was approximately 50 ng per plant.

TABLE 5

Fruit Weight (Gram/Plant)

| | Treatments | | | |
|---|---|---|---|---|
| Base | 0 ng | 10 ng | 50 ng | 100 ng |
| Water | 92.81 | 96.11 | 108.99 | 88.57 |
| Bacterial Carrier | 74.14 | 97.97 | 103.32 | 66.26 |
| Bacterial Supernatent | 61.65 | 67.2 | 100.48 | 109.13 |
| Mean | 76.2 | 87.09 | 104.26 | 87.99 |

Notes;
See Table 3 above.

There was statistically significant effect between 50 ng LCO treatment and control on fruit weight of Cobra. 50 ng treatment showed more uniform result in different delivery medium. The increase of early yield by 50 ng LCO showed the potential ability of LCO applied as a growth enhancer on tomatoes. Water was the optimal carrier for LCO application in this study.

Experiments 1 and 2

Summary of the Experiment: Effect of LCO on Tomato Flowering

Two experiments were performed to investigate effect of LCO on plant's flowering using greenhouse-grown tomato plants.

In general, LCO induced early flowering in both experiments (FIGS. 8 and 9).

Experiment 1

LCO treatment induced flowering in 25% more plants as compared to control at day 1 of assessment. This increase was sustained thorough out experiment, reaching 35% difference at day 4 of assessment. LCO treatment caused a 3 day-shift in time of flowering, i.e., over 80% of LCO treated plants flowered 3 days earlier than control, non-treated plants. Early flowering will initiate earlier fruit set and subsequent earlier fruit development, which in turn leads to higher yield of tomatoes.

Experiment 2

Initial assessment of tomato flowering confirmed again that LCO treatment induces early flowering in tomatoes. Initially, there is a 10% difference between LCO treated plants and control. This difference increased to 20% by day 3 of assessment. Initial data obtained in this experiment confirms findings from previous one and further supports claim that LCO treatment incuses early flowering in plants.

Experiments 3 and 4

Summary of the Experiment: Effect of LCO on Flowering in *Arabidopsis thaliana*

Two experiments were performed to investigate effect of LCO on plant's flowering using experimental model plant *Arabidopsis thaliana*.

In general, LCO induced early flowering in both experiments (FIGS. 9 and 10).

Plants were treated with various a range of LCO concentrations. It was found that treatment with $10^{-7}$ Molar the most effective in induction of flowering. The LCO treated plants reached over 80% of plants with open flowers 4 days earlier than control, surfactant treated plants. LCO induced faster and more uniform flowering.

Experiment 5: Foliar Application of LCO to Bedding Plants

This is a growth room study. Seeds of garden plant species were selected on the basis of seed-purchase popularity (Norseco, Montreal), grown in trays of Pro-Mix (NB. trademarked name) Seeding Medium, and at some size were transplanted into trays of 36 and 32 wells containing the same medium. Growth proceeded under lights in the growth room.

Some 2 weeks before expected flowering, 16 young plants were sprayed with each of various levels of LCO leaving control plants untreated. The results are presented in Table 5A on bud formation and where possible opened flowers.

TABLE 5A

Effect of LCO Application on ornamental plants

| Treatments | Total Number of Impatiens buds | Total Number of Marigold buds |
|---|---|---|
| Untreated Conrol | 68 | 26 buds and 1 flower |
| 20 ml/16 plants of $10^{-7}$M LCO application | 71 | 26 buds and 0 flower |
| 50 ml/16 plants of 3 × $10^{-5}$M LCD application | 66 | 34 buds and 3 flowers |
| 20 ml/16 plants of $10^{-3}$M LCO application | 85 | 24 buds and 1 flower |
| 20 ml/16 plants of $10^{-3}$M LCO application | 65 | 25 buds and 2 flower |

It was also noted that with Marigolds all the LCO treatments produced some plants with 3 flower buds and the 50 ng treatment had some (2) with 4 flower buds per plant. No untreated control plant had more than 2 buds per plant.

Trial 3: Flowering and Yield Benefit from Foliar Application of LCO

Summer Field Trial at Macdonald College Research Farm

An investigation was conducted to examine whether foliar applications of LCO led to increased yield in tomato crop production. To determine concentrations or strengths to be applicable, testing was conducted with a logarithmic increase in strength from 1 nanogram (ng) to 1000 ng/plant sprayed once, and on half, twice.

Figure 12B:
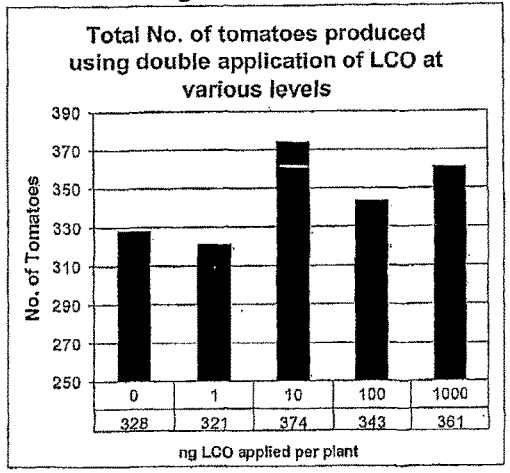
Figure 13A:
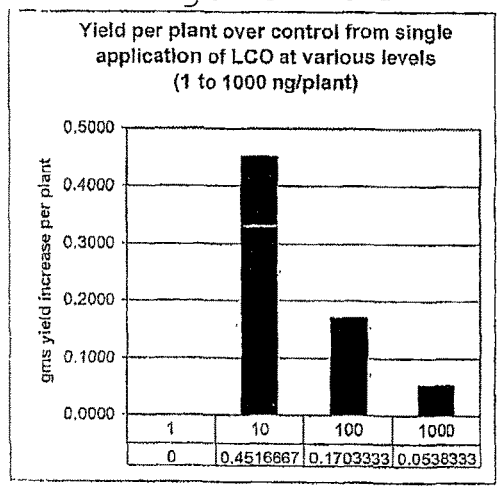
FIGS. 13A and 13B show (A) Yield per plant over control from a single application of LCO at various levels (1 to 1000 ng/plant), and (B) yield response due to 2nd application of LCO.
Figure 13B:
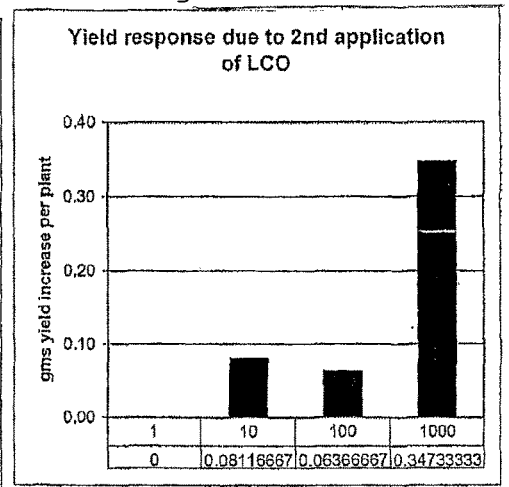

The trial results are presented in the following FIGS. 11-13 and Tables 6 and 7. The parameter of interest was ripened fruit which was harvested 2 or 3 times a week, recording each time, both fruit weight and number of fruit per set of replicates. It was known that fruit arise from pollinated flowers and that an increase in the one leads to the other. FIG. 11 records, cumulative harvested (red) fruit per treatment. For the single LCO application it will be seen that the 10 and 100 ng/plant treatments have advanced fruiting by some 10 days over control (horizontal separation in weeks). That advance has allowed the plant to bear and ripen more fruit over the season for these treatments (see FIG. 11 note height over control and Tables 6 and 7 for actual weights and numbers harvested). Table 6 and FIG. 12 record harvested weight and numbers of ripened fruit over season and it can be seen that the average weight of the tomatoes is not different between treatments and control. Thus the increase in harvested weight was due to an increase in numbers harvested, in agreement with actual enumeration. Table 7 and FIG. 13 demonstrate that the yield increase over the season was a statistically significant 17% for single application of 10 ng LCO/plant and agrees with Table 6 where numbers for this application were similarly increased—some 20%.

Fruit numbers in treated plants are increased by 17%-20% arising from a similar increase in numbers of flowers able to be pollinated.

From FIG. 11 there is a shift to earlier flowering when plants are treated with LCOs at specific concentrations, the concentrations required for physiological change being typical of a phytohormone where a very narrow range of concentration at very low concentrations is of benefit—higher and lower concentrations have no effect.

Second applications are similar in trend but less clear in analysis because the second application led to a later increase in unharvestable green fruit stopped from ripening by impending frost. This would not be a problem in greenhouse operations where this indeterminate plant continues to yield over many months as long as root fed.

TABLE 7

LCO on Tomatoes
Cumulative yield data to Sept. 23
Each data point is the average of 4 randomized rows, each of 6 plants
Yield in kg per plant

| ng LCO per plant | Harvest Cumulative Harvest to Sept 23. | | No. of Applications | | | | |
|---|---|---|---|---|---|---|---|
| | Applied once | Applied Twice | Yield increase over Control | | Yield Increase | Percent Yield Inc. over Control | |
| | (24 plant Average) | (24 plant Average) | Applied once | Applied Twice | for 2 nd Application | Applied once | Applied Twice |
| 1 | Not as good as Control | 0.0000 | — | 0.00 | — | — | |
| 10 | 3.0093 | 3.0905 | 0.4517 | 0.3452 | 0.08 | 17.7% | 12.6% |
| 100 | 2.7280 | 2.7917 | 0.1703 | 0.0403 | 0.06 | 6.7% | 1.7% |
| 1000 | 2.6115 | 2.9588 | 0.0538 | 02135 | 0.35 | 2.1% | 7.8% |
| control-Water | 2.5577 | 2.7453 | — | — | 0.19 | — | — |

Experiment 6: Foliar Application of LCO at Variable Growth Stages

TABLE 2-1

Response Of Tomato Fruit Yield To LCO Foliar Application At Variable Growth Stages

| LCO Applied Time | Fruit on 24 plants | Weight (kg) per 24 plants | Average Weight (g/fruit) | Fruit # % vs. control | % of weight vs. control |
|---|---|---|---|---|---|
| 10 DATP* (7/4) | 1276ab | 150.88ab | 118.2 | 28.63 | 10.8 |
| 20 DATP (7/15) | 1260ab | 163.78ab | 130.0 | 27.02 | 20.3 |
| 30 DATP (7/25) | 1199abc | 160.11ab | 133.5 | 20.87 | 17.6 |
| 40 DATP (8/8) | 1318ab | 155.89ab | 118.3 | 32.86 | 14.5 |
| 50 DATP (8/18) | 1115bc | 154.62ab | 138.7 | 12.40 | 13.6 |
| 10 + 20 DATP (7/4 + 7/15) | 1125bc | 153.43ab | 136.4 | 13.41 | 12.7 |
| 10 + 20 + 30 DATP (7/04 + 7/15 + 7/25) | 1282ab | 161.89ab | 126.3 | 29.23 | 18.9 |
| 10 + 20 + 30 + 40 DATP (7/4 + 7/15 + 7/25 + 8/7) | 1191abc | 152.50ab | 128.0 | 20.06 | 12.0 |
| 10 + 20 + 30 + 40 + 50 DATP (7/4 + 7/15 + 7/25 + 7/8 + 8/18) | 1373a | 174.07a | 126.8 | 38.41 | 27.8 |
| Untreated control (UC) | 992c | 136.15b | 137.3 | 0 | 0 |
| Significance at 5% | Yes | Yes | No | No | No |

*DATP standards for Days After Transplanting

Tomato seedlings (6-leaf stage) were transplanted in farmland. The plants were watered on the day that they were transplanted and whenever the soil was very dry during the season. Fertilizer (20-20-20) was applied at 250 kg/ha to the tomato field before transplantation. All tomato plants were supported by sticks when they were heavily loaded with fruit. Fruit yield (in the table) was finally cumulated at the end of the season.

Compared to the untreated control, LCO increased fruit number (up to 38.4%) and total fruit weight (up to 27.8%). Five of 9 treatments had significantly increased fruit number over control. For a single application of LCO, the best time is 20-40 days after transplantation. Multiple applications led to increased fruit yields over a single application but these results were not significantly significant.

Experiment 7: Foliar Application of LCO on Pepper

TABLE 2-2

Effect Of LCO Foliar Application On Pepper Early Fruit Maturity (Sept. 17) And Final Yield (Oct. 9) In Horticulture Centre 2003.

| | First 4 wk yield | |
|---|---|---|
| Treatments | Fruit/plant | gram/plant |
| 14 ng/plant | 5.79ab | 784.91ab |
| 50 ng/plant | 5.83ab | 833.79ab |
| 75 ng/plant | 5.77ab | 835.26ab |
| 100 ng/plant | 4.87b | 694.48b |
| 141 ng/plant | 6.48a | 934.83a |
| 282 ng/plant | 5.02ab | 702.87b |
| Water | 4.87b | 643.37b |
| Significant at 5% | Yes | Yes |

13 pepper seedlings (cv. Camelot, 6-leaf stage) were transplanted in 2 rows per plot (3.5×2.5M$^2$). The rows were covered with 65 cm width black plastic mulch one week before transplanting. Fertilizer (10-52-10) solution of 250 ppm was applied into the planting hole through the mulch when transplanting (approx. 250 ml per plant). The drip irrigation system was set to twice a week and 4 hours each time, depending on the soil moisture. Plants were sprayed with LCO 14 days after transplanting (5 ml/plant) and 27 days after transplanting (50 ml/plant).

LCO foliar application significantly increased fruit number in the early stages by approximately 1 fruit per plant. Treatment of 141 ng/plant (5 ml of 2×10$^{-8}$M) was the best dose.

Experiment 8: Foliar Application of LCO on Corn

TABLE 2-3

Effect Of Foliar Application Of LCO On Sweet Corn Ear Number

| Treatments | Ears/ha | Ear Weight (kg)/ha | Marketable ears/ha | Average Length(cm)/ear | Ear No/plant |
|---|---|---|---|---|---|
| 10$^{-7}$M once | 65416.7 ab | 4383.3 | 25000.0 | 13.12 c | 0.934 |
| 10$^{-8}$M once | 67083.3 ab | 4800.0 | 26250.0 | 13.24 bc | 0.905 |
| 10$^{-9}$M once | 68333.3 a | 4266.7 | 29166.7 | 13.68 abc | 0.928 |
| 10$^{-7}$M twice | 70833.3 a | 5000.0 | 30416.7 | 13.81 ab | 0.935 |
| 10$^{-8}$M twice | 62083.3 ab | 5150.0 | 30000.0 | 13.64 abc | 0.856 |
| 10$^{-9}$M twice | 56666.7 bc | 4033.3 | 25000.0 | 13.43 bc | 0.886 |
| Water Control | 49166.7 c | 4416.7 | 39583.3 | 14.23 a | 0.760 |
| Sigtlificance | P < 0.05 | NS | NS | P < 0.05 | NS |

Fertilizer (36-12-18) was applied to the corn field at 500 kg/ha before seeding. A machine planter was employed to sow sweet corn grain. Plot size was 4×4.5=18 M$^2$, and 6 rows/plot. To protect corn ears from raccoons and other animal damage, sweet corn plants were protected with an electric fence around the plots after silking. LCO was applied once 40 days after sowing or/and twice, 40 days after sowing and 58 days after sowing at a rate of 200 L/ha for the first application and 300 L/ha for the second application. Corn was harvested 80 days after sowing, from the two middle rows and corn ears reaching 12 cm or longer were counted as marketable.

Foliar application of LCO in the range of 10$^{-8}$-10$^{-7}$M significantly increased total number of sweet corn ears. Total ear weight and marketable ear number were not increased by the treatments in these experiments as it was necessary to harvest the crop before all were fully ripened.

Experiment 9: Effect of LCO on Grain Corn Yield

TABLE 2-4

Effect of foliar application of LCO on the fresh and dry yield of grain corn

| Treatments | Fresh Yield (kg/2 rows) | Fresh Yield (kg/ha) | Dry Yield kg/2 rows) | Dry yield (kg/ha) | Ears/2 rows |
|---|---|---|---|---|---|
| 10$^{-7}$M once | 4.40 | 7333.3 | 3.44 | 5730.6 | 37.25ab |
| 10$^{-8}$M once | 4.57 | 7616.7 | 3.62 | 6040.4 | 37.00ab |
| 10$^{-9}$M once | 4.75 | 7916.7 | 3.77 | 6275.6 | 39.00ab |
| 10$^{-7}$M twice | 5.03 | 8383.3 | 3.96 | 6606.5 | 40.00a |
| 10$^{-8}$M twice | 4.12 | 6866.7 | 3.23 | 5387.1 | 32.25bc |
| 10$^{-9}$M twice | 4.55 | 7583.3 | 3.57 | 5953.5 | 37.25ab |
| Water Control | 4.26 | 7100.0 | 3.38 | 5637.6 | 32.00c |
| Significance | NS | NS | NS | NS | P < 0.05 |

Fertilizer (36-12-18) was applied to the corn field at a rate of 500 kg/ha before seeding. A machine planter was employed to plant the grain (cv. DK376, HU2650, Fludioxnil coated). To protect corn ears from bird damage, grain corn ears in the middle two rows were covered with plastic nets after silking. LCO was applied to corn plants at a rate of 200 L/ha for the first application 40 days after planting and at 400 L/ha for the second application 58 days after planting. The two protected middle rows of plants were harvested by a combine 152 days after planting. Ear number was significantly increased by all treatments of LCO application over untreated control, except for the 10$^{-8}$M double application. The total grain yield increased for all but the 10$^{-8}$M double application.

Experiment 10: Effect of LCO on Ridgetown Tomato

TABLE 2-5

Effect Of LCO Application On Ridgetown Canning Tomato (The First Harvesting Data)

| Treatments | Fruit number on 24 plants) | Increase vs. CK (%) | Fruit weight (kg/24 plants) | Increase vs. CK (%) |
|---|---|---|---|---|
| 50-0-0 | 206AB | 12.6% | 11.916 | 9.9% |
| 0-50-0 | 209AB | 14.2% | 12.598 | 16.2% |
| 50-50-0 | 219A | 19.7% | 12.567 | 15.9% |
| 50-75-0 | 199AB | 8.7% | 11.421 | 5.3% |
| 0-50-75 | 191AB | 4.4% | 11.352 | 4.7% |
| Control | 183B | 0 | 10.844 | 0 |
| Significant at 5% | Yes | | No | |

The experiment was conducted at Ridgetown College, University of Guelph, Ridgetown, Ontario. Tomatoes were transplanted in single twin rows, 7 m in length spaced 1.65 m apart. Treatments of LCO were applied three times, two weeks before flowering (28 days after transplant), two weeks after flowering (52 days after transplant) and six weeks after flowering (69 days after transplant). Spray applications were applied using a specialized, small plot research CO$_2$ sprayer with a two-nozzled, hand-held boom applying 200 L/ha of spray. Rates were determined based on 38 tomato plants per plot, replicated 4 times, equaling 152 plants per treatment. Early fruit was harvested for yield evaluation on Aug. 20, 2003. LCO foliar spray applied to tomato plants at 2 weeks before and after flowering significantly increased fruit number by up to 20% and also increased fruit weight by up to 16%.

Experiment 11: LCO Foliar Application in Greenhouse Tomatoes

Tomatoes were seeded and transplanted into 10" pots 30 days later in the greenhouse. Plants were sprayed with 5 ml (50 ng) LCO solution per plant 10 days after transplant and 14 days after transplant (50 ng×2). Flowering data was collected 28 days after transplant.

LCO improved tomato early flowering, and a 50 ng/plant single application better than a double application. All applications were better than control. See FIG. 2-1.

The same plants as FIG. 2-1 were sampled for fruit data 28 days after transplant.

There were no fruit seen on the control plants at this moment, however, foliar application of LCO increased tomato early fruit setting under greenhouse conditions. Treatment of a single 50 ng LCO application increased fruit set by approx. 1 fruit/plant. See FIG. 2-2.

Experiment 12: LCO Application on Marigolds

Marigolds were planted in 32-cell flat and LCO was applied foliarly to plants 4 weeks after sowing (4 flats/treatment, 1 ml/plant applied containing various levels of LCO). Data collection started from the first flower appearing.

The higher doses of LCO (100-200 ng/plant) enhanced flowering in the first 2 weeks after application, whereas the lower doses (10-50 ng/plant) showed better enhancement of flower 3 weeks after application. The best treatments advanced flowering by 2 days and the number of flowers at 25 days by 8%. See FIG. 2-3.

Experiment 13: LCO Application on Strawberries

Field strawberries were sprayed with a foliar application of LCO at three dosages on the same day, as set out in FIG. 2-4. Fruit was harvested 2-3 times a week, beginning 24 days after application.

Treatment of LCO at 10-8 M (70 ng/plant) increased early fruit setting and fruit number 3-7 weeks after application from 7 to 30%.

Experiment 14: LCO Application on Cherry Tomatoes

Cherry tomato seedlings (5-week old) were transplanted into 5" pots in the greenhouse. LCO solutions were prepared with water and 50 ml/plant was applied to the soil in the pot after transplantation. Ripened fruit (orange or red) were collected 8 weeks after transplantation.

LCO soil applied to transplanted cherry tomato enhanced early fruit number. LCO 10 ng per plant by soil application showed the best fruit enhancement at the early stage. See FIG. 2-5.

Experiment 15: LCO Application on Early Fruit Number and Yield

Red tomato seedlings (cv. Mountain Spring) were transplanted at their 4-leaf stage. 7 plants in one row were transplanted in each plot of 3.5×2.5M2. The row was covered with 65 cm width black plastic mulch, one week before transplanting. Fertilizer (10-52-10) solution of 250 ppm was applied into the planting hole through the mulch when transplanting (approx. 250 ml/plant). the drip irrigation system was set to twice a week and 4 hours each time, depending on the soil moisture. Plants were sprayed with LCO 15 days after transplant (5 ml/plant) and 29 days after transplant (20 ml/plant). Fruits were first harvested 67 days after transplant.

LCO application significantly increased early fruit number and weight, but did not increase the average fruit size. The optimal application was 75 ng/plant. See FIGS. 2-6 and 2-7.

Experiment 16: LCO Application on Fruit Number and Weight at End of Season

Tomato seedlings (6 leaf-stage) were transplanted. The plants were watered on the day they were transplanted and whenever the soil was very dry during the season. Fertilizer (20-20-20) was applied at 250 kg/ha to the tomato field before transplantation. All tomato plants were supported with sticks when they were heavily loaded with fruit. Fruit yield was finally cumulated at the end of the season 115 days after transplant.

Data showed the optimal application was 20-40 days after transplantation. During this period, LCO applied once at 50 ng increased fruit number by up to 33% and fruit weight by up to %. See FIGS. 2-8 and 2-9.

Experiment 17: Effect of LCO on Hot Pepper Flowering and Fruiting 30-day old seedlings were transplanted into 5" pots and 20 days later (20 DAT) plants received the first LCO spray at 2 ml/plant (50 ng/plant). The 2nd spray was conducted 3 weeks (41 DAT) after the first. Data was collected 5 weeks (55 DAT) after the first LCO application.

LCO applied in single or double applications increased early flowers up to 5% and 40% over control, respectively at 5 weeks. See FIGS. 2-10 and 2-11.

30-day old seedlings were transplanted into 5" pots and 20 days later (20 DAT) plants received the first LCO spray at 2 ml/plant (50 ng/plant). The 2nd spray was conducted 3 weeks (41 DAT) after the first. Data was collected 5 weeks (55 DAT) after the first LCO application.

LCO applied in single or double applications increased the number of early fruits by up to 159% o and 284% over control, respectively, in 5 weeks. See FIG. 2-11.

Experiment 18: LCO Application on Legume

TABLE 8

Effect of LCO foliar application on grain yield and biomass of Legumes

| Treatments | Biomass (g/5-plant) | | Yield (kg/ha) | |
| --- | --- | --- | --- | --- |
| | Applied once | Applied twice | Applied once | Applied twice |
| LCO 1 ng | 49.46 AB | 55.10 AB | 2563.96 AB | 2673.54 AB |
| LCO 10 ng | 46.28 AB | 60.11 A | 2515.33 B | 2385.75 B |
| LCO 100 ng | 46.87 AB | 55.09 AB | 2635.00 AB | 2974.17 A |
| LCO 1000 ng | 47.99 AB | 47.81 AB | 2452.71 B | 2620.42 AB |
| Water | 45.07 B | 55.13 AB | 2293.25 B | 2421.88 B |
| Untreated control | 1.1.1 | N/A | 1.1.2 | 2285.33 B |

A short heat-unit variety of soybean (cv. Nortman, HU 2425) was planted at density of plants on the field of approx. 300 plants per plot (500,000 plants/ha). The soybean plants were first treated with LCO at their blooming stage 24 days after planting. The treatment amounts of LCO (detailed above) were diluted with distilled water to give a 2-liter solution sprayed over 4 plots of the treatment. The second application was sprayed at the podding stage 49 days after planting. As before, the LCO was diluted with distilled water to 2-liter solution per 4 plots of the treatment. The plants receiving a single application were sprayed with LCO for the first time, whereas the plants receiving a double application were sprayed for the second time. A $CO_2$ pressure sprayer was employed for this trial. The amount of fluid dispensed by the sprayer was controlled by the nozzle size. It was calibrated with water prior to spraying with LCO. Biomass was examined 58 days after planting by digging out by hand 5 plants per plot. The final yield was obtained by harvesting by combine the intact area (2-meter long to the end) 101 days after planting. The data were analyzed with the SAS program.

Although the present invention has been described hereinabove by way of preferred embodiments thereof, it can be modified, without departing from the spirit and nature of the subject invention as defined in the claims hereafter.

COs and associated enhancement of growth and yield.

The invention claimed is:

1. A method of initiating early flowering and/or fruiting in a non-leguminous plant, comprising foliarly applying to said plant, prior to flowering and/or fruiting of said plant, at least one lipo-chitooligosaccharide (LCO) to said plant in an amount effective to initiate early flowering and/or fruiting in said plant.

2. The method of claim 1, wherein said plant is of the family Brassicaceae, Solonaceae, Chenopodiceae, Asteraceae, Malveceae, Cucurbutaceae, or Poaceae.

3. The method of claim 1, wherein said plant is a corn plant.

4. The method of claim 1, wherein said plant is a tomato plant.

5. The method of claim 1, wherein said plant is a pepper plant.

6. The method of claim 1, wherein said plant is a strawberry plant.

7. The method of claim 1, wherein said at least one LCO is applied at a concentration ranging from about $10^{-9}$ M to about $10^{-7}$ M.

8. The method of claim 1, wherein said at least one LCO is applied in an amount ranging from about 10 ng to about 1000 ng.

9. The method of claim 1, wherein said at least one LCO is applied in an amount ranging from about 10 ng to about 100 ng.

10. The method of claim 1, wherein said at least one LCO is applied in an amount ranging from about 10 ng to about 200 ng.

11. The method of claim 1, wherein said at least one LCO is applied in an amount ranging from about 100 ng to about 1000 ng.

12. The method of claim 1, wherein said at least one LCO is applied about 40 to about 60 days after sowing said plant.

13. The method of claim 1, wherein said plant exhibits early budding as compared to an untreated control plant.

14. The method of claim 1, wherein said plant exhibits early flowering as compared to an untreated control plant.

15. The method of claim 1, wherein said plant exhibits early fruiting as compared to an untreated control plant.

16. The method of claim 1, wherein said plant is a corn plant and wherein said at least one LCO is applied at a concentration ranging from about $10^{-9}$ M to about $10^{-7}$ M.

17. The method of claim 1, wherein said plant is a tomato plant and wherein said at least one LCO is applied in an amount ranging from about 10 ng to about 1000 ng.

18. The method of claim 1, wherein said plant flowers at least two days earlier than an untreated control plant.

19. The method of claim 1, wherein said plant flowers at least three days earlier than an untreated control plant.

20. The method of claim 1, wherein said plant flowers at least four days earlier than an untreated control plant.

21. The method of claim 1, wherein said plant fruits at least 8 days earlier than an untreated control plant.

* * * * *